(12) United States Patent
Bagherinia

(10) Patent No.: US 10,123,691 B1
(45) Date of Patent: Nov. 13, 2018

(54) METHODS AND SYSTEMS FOR AUTOMATICALLY IDENTIFYING THE SCHWALBE'S LINE

(71) Applicant: Carl Zeiss Meditec, Inc., Dublin, CA (US)

(72) Inventor: Homayoun Bagherinia, Oakland, CA (US)

(73) Assignee: CARL ZEISS MEDITEC, INC., Dublin, CA (US)

(*) Notice: Subject to any disclaimer, the term of this patent is extended or adjusted under 35 U.S.C. 154(b) by 0 days.

(21) Appl. No.: 15/458,393

(22) Filed: Mar. 14, 2017

Related U.S. Application Data

(60) Provisional application No. 62/308,478, filed on Mar. 15, 2016.

(51) Int. Cl.
| | | |
|---|---|---|
| *A61B 3/00* | (2006.01) | |
| *A61B 3/14* | (2006.01) | |
| *A61B 3/10* | (2006.01) | |
| *A61B 3/117* | (2006.01) | |
| *G06T 7/60* | (2017.01) | |
| *G06T 7/00* | (2017.01) | |

(Continued)

(52) U.S. Cl.
CPC ............ *A61B 3/0025* (2013.01); *A61B 3/102* (2013.01); *A61B 3/117* (2013.01); *G06T 7/0012* (2013.01); *G06T 7/11* (2017.01); *G06T 7/60* (2013.01); *G06T 5/002* (2013.01); *G06T 2207/10101* (2013.01); *G06T 2207/30041* (2013.01)

(58) Field of Classification Search
CPC .. A61B 3/102; A61B 3/14; A61B 3/12; A61B 3/113; A61B 3/0025

USPC .................................................. 351/200–246
See application file for complete search history.

(56) References Cited

U.S. PATENT DOCUMENTS 8,687,866 B2 * 4/2014 Marziliano ............... G06T 7/75
356/497
2007/0291277 A1 12/2007 Everett et al.
(Continued)

OTHER PUBLICATIONS

Jing et al., "Automatic Detection of Schwalbe's Line in the Anterior Chamber Angle of the Eye using HD-OCT Images", 32nd Annual International Conference of the IEEE EMBS, Aug. 31-Sep. 4, 2010, pp. 3013-3016.

(Continued)

*Primary Examiner* — Mohammed Hasan
(74) *Attorney, Agent, or Firm* — Morrison & Foerster LLP

(57) ABSTRACT

Various methods for automatically identifying the Schwalbe's line location in an optical coherence tomography (OCT) image of the anterior chamber of an eye are described. In one example method, the posterior corneal surface in the ROI is segmented by using one or more segmentation approaches to produce a segmented output. A curvature is computed at each segmented point to identify a set of local curvature maxima locations. Features at each local curvature maxima location are evaluated. The Schwalbe's line location is identified using the evaluated features at each maxima location. Other methods for identifying the Schwalbe's line location discussed in the present application are based on identification of a location of maximum curvature in the curvature function and identification of a maximum distance to the convex-hull of a model fit.

18 Claims, 14 Drawing Sheets

(51) Int. Cl.
*G06T 7/11* (2017.01)
*G06T 5/00* (2006.01)

(56) References Cited

U.S. PATENT DOCUMENTS

| 2012/0140174 A1* | 6/2012 | Hee ................. A61B 3/0025 |
| | | 351/206 |
| 2013/0188140 A1 | 7/2013 | Bagherinia et al. |
| 2013/0208240 A1 | 8/2013 | Sharma et al. |

OTHER PUBLICATIONS

Lee et al., "Association Between Baseline Angle Width and Induced Angle Opening Following Prophylactic Laser Peripheral Iridotomy", IOVS, vol. 54, No. 5, May 2013, pp. 3763-3770.
Qin et al., "Anterior Chamber Angle Measurements Using Schwalbe's Line with High Resolution Fourier-Domain Optical Coherence Tomography", J Glaucoma, vol. 22, No. 9, Dec. 2013, 13 pages.
Soille, P., "Morphological Image Analysis: Principles and Application", Second Edition, Springer, 1999, pp. 173-174.
Timp et al., "A New 2D Segmentation Method Based on Dynamic Programming Applied to Computer Aided Detection in Mammography", Medical Physics, vol. 31, No. 5, May 2004, pp. 958-971.
Tomasi et al., "Bilateral Filtering for Gray and Color Images", Proceedings of the 1998 IEEE International Conference on Computer Vision, 1998, 8 pages.
Vincent, Luc, "Morphological Grayscale Reconstruction in Image Analysis: Applications and Efficient Algorithms", IEEE Transactions on Image Processing, vol. 2, No. 2, Apr. 1993, pp. 176-201.

\* cited by examiner

FIG. 1 (Prior-art)

FIG. 2 (Prior-art)

METHODS AND SYSTEMS FOR AUTOMATICALLY IDENTIFYING THE SCHWALBE'S LINE

PRIORITY

The present application claims priority to U.S. Provisional Application Ser. No. 62/308,478 filed Mar. 15, 2016, the contents of which are hereby incorporated by reference.

BACKGROUND

Glaucoma is one of the major eye diseases globally and causes irreversible loss of vision due to the optic nerve damage leading to blindness. It is largely caused by poor filtration of aqueous fluid in the eyeball through the anterior chamber angle. If untreated, it leads to higher internal pressure, permanent nerve damage, and blindness. There are two main types of glaucoma, depending on how the flow of fluid is blocked. These are 1) open-angle glaucoma, which is caused by a gradual hype-functioning of the trabecular meshwork, and 2) angle-closure glaucoma (ACG), which is caused by a change in the position of the iris, which then occludes the drainage channels.

Detection of ACG in the early stage could lead to treatment to arrest its development or slow down the progression. One of the ways of detecting the ACG is anterior chamber angle assessment or measuring the Iridocorneal angle using landmarks such as Schwalbe's line and the Scleral spur. Iridocorneal angle measurements can help to determine suitability of implantable device(s) within the Iridocorneal angle for treating ACG in patients. It is important that these device(s) be implanted in a way that does not harm the corneal endothelium. By ensuring that the largest footprint of the implant would not reach the Schwalbe's line, a physician can confirm that an eye has a configuration suitable for the implant.

In the past, ACG has been diagnosed from optical coherence tomography (OCT) images by finding the scleral spur and assuming a fixed length of the trabecular meshwork (see for example, Lee, R. Y., et al. (2013). "Association between baseline angle width and induced angle opening following prophylactic laser peripheral iridotomy." *Invest Ophthalmol Vis Sci* 54(5): 3763-3770). This method was developed when anterior segment OCT used a 1300 nm wavelength, so the scleral spur was generally well seen. The majority of commercial OCT instruments are currently using a wavelength of 840 nm, which has worse penetration through the sclera and much poorer visualization of the scleral spur than an OCT with a 1300 nm wavelength. Some have proposed that since Schwalbe's line is easier to see than the scleral spur in such OCT images, this landmark could be used, again with a fixed length assumed for the trabecular meshwork (see for example, T. Jing, P. Marziliano and H. T. Wong, "Automatic detection of Schwalbe's line in the anterior chamber angle of the eye using HD-OCT images," *Engineering in Medicine and Biology Society (EMBC)*, 2010 *Annual International Conference of the IEEE*, Buenos Aires, 2010, pp. 3013-3016, hereby incorporated by reference).

FIG. 1 shows an exemplary anterior segment high definition optical coherence tomography (HD-OCT) image (referred to herein simply as an OCT image throughout the present disclosure). It is marked to illustrate the locations of the angle recess (the region between the cornea and the iris), the scleral spur (the point where the curvature of the angle wall changes), the corneal endothelium (inner-most layer of cornea), the corneal epithelium (the inner-most layer of cornea), Descemet's membrane (the second innermost layer), and Schwalbe's line (the termination of Descemet's membrane). As illustrated in FIG. 1, the angle recess is obscured in shadow and the scleral spur is not well defined in the OCT image due to the scattering by the sclera. On the other hand, Schwalbe's line, which marks the termination of Descemet's membrane can be identified more clearly in most of the OCT images.

Since the scleral spur is harder to detect, an automatic detection of Schwalbe's line is an alternative landmark to measure the Iridocorneal angle. One of the existing methods to automatically identify the Schwalbe's line (U.S. Pat. No. 8,687,866, hereby incorporated by reference) includes 1) segmenting the posterior corneal surface, 2) extracting the edge of the cornea using linear regression, and 3) using the point at which there is maximum distance between the points on the cornea and the regression line as the location of Schwalbe's line, as shown in FIG. 2. However, there are various limitations associated with this method. Some of them are: 1) in an occurrence of a segmentation error, identifying the Schwalbe's line location based on the maximum distance between the points on the cornea and the regression line is not reliable. For instance, due to the segmentation error, the maximum distance and the regression line may be at different location than the location of the Schwalbe's line. By way of an example, vertical shadows due to eye-lid scans at posterior surface make the segmentation unreliable. Other limitations of this prior-art method are that 2) the method uses a single fitting model, which may not be robust due to variation in anatomy, and 3) the regression line can be biased towards noise (i.e., segmentation error(s)).

Here we describe new methods for automatically detecting the Schwalbe's line that overcomes one or more limitations of the previous/existing methods as discussed above.

SUMMARY

According to one aspect of the subject matter described in the present application, a method to automatically identify Schwalbe's line location in an OCT image of the anterior chamber of an eye includes acquiring measurements of the eye with an OCT device; generating an OCT image from the measurements; segmenting the posterior corneal surface in the image by using one or more segmentation approaches to produce a segmented output; evaluating features at each local location on the posterior surface of the cornea where at least one feature includes the local curvature; identifying the Schwalbe's line location using the evaluated features at each maxima location; and storing or displaying the identified Schwalbe's line location or a further analysis thereof.

According to another aspect of the subject matter described in the present application, a method to automatically identify Schwalbe's line location in an OCT image of the anterior chamber of an eye includes acquiring measurements of the eye with an OCT device; generating an OCT image from the measurements; segmenting the posterior corneal surface in the image by using one or more segmentation approaches to produce a segmented output; fitting a plurality of different models to the segmented output; selecting a model from the plurality that is best suited for the Schwalbe's line identification based on one or more metrics; computing a curvature function of the selected model; identifying the location of maximum curvature as the Schwalbe's line location; and storing or displaying the identified Schwalbe's line location or a further analysis thereof.

According to yet another aspect of the subject matter described in the present application, a method to automatically identify Schwalbe's line location in an OCT image of the anterior chamber of an eye includes acquiring measurements of the eye with an OCT device; generating an OCT image from the measurements; extracting a region of interest (ROI) in the OCT image where the Schwalbe's line is expected to be located; segmenting the posterior corneal surface in the ROI by using one or more segmentation approaches to produce a segmented output; fitting a plurality of different models to the segmented output; selecting a model from the plurality that is best suitable for the Schwalbe's line identification based on one or more metrics; determining the convex-hull of the fit of the selected model; identifying a point of maximum distance between the edges of the convex-hull below the model fit and the model fit as the Schwalbe's line location; and storing or displaying the identified Schwalbe's line location or a further analysis thereof.

According to yet another aspect of the subject matter described in the present application, a method to automatically identify Schwalbe's line location in an OCT image of the anterior chamber of an eye includes acquiring measurements of the eye with an OCT device; generating an OCT image from the measurements; segmenting the posterior corneal surface in the image by using one or more segmentation approaches to produce a segmented output; fitting a plurality of different models to the segmented output; identifying locations of maximum curvature for each model; determining Schwalbe's line from the set of maxima using machine learning; and storing or displaying the identified Schwalbe's line location or a further analysis thereof.

Further aspects include various additional features and operations associated with the above and following aspects and may further include, but are not limited to corresponding systems, methods, apparatus, and computer program products.

The features described herein are not all-inclusive and many additional features will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 10A shows curvature function upon fitting a third degree polynomial to the segmentation. FIG. 10B shows curvature function upon fitting a fifth degree polynomial to the segmentation and FIG. 10C shows curvature function upon fitting a thirteenth degree polynomial to the segmentation.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirely.

Example OCT System

Figure 3:
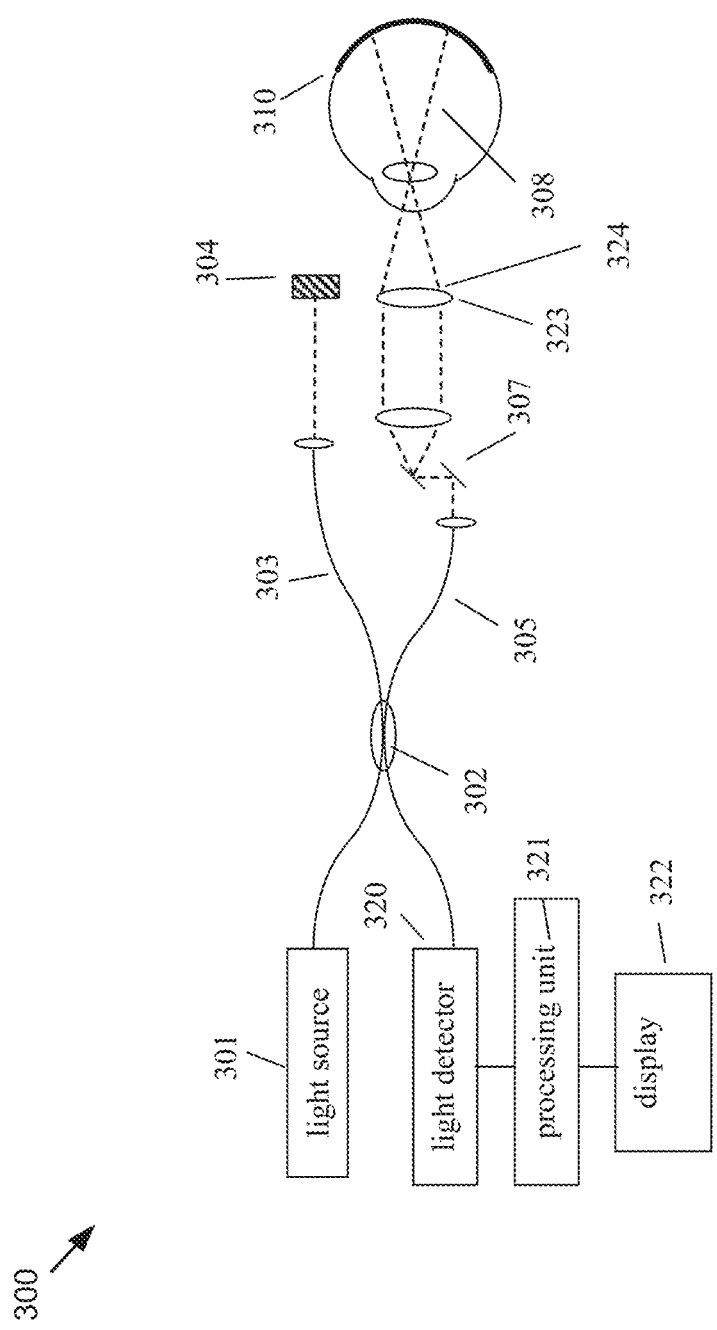
FIG. 3 is a generalized optical coherence tomography (OCT) system that can be used to practice the present invention.

A generalized FD-OCT system 300 used to collect 3-D image data of the eye suitable for use with the present invention is illustrated in FIG. 3. The system 300 includes a light source, 301, typical sources including but not limited to broadband light sources with short temporal coherence lengths or swept laser sources. A beam of light from source 301 is routed, typically by optical fiber 305, to illuminate the sample 310, a typical sample being tissues in the human eye. The source 301 can be either a broadband light source with short temporal coherence length in the case of SD-OCT or a wavelength tunable laser source in the case of SS-OCT. The light is scanned, typically with a scanner 307 between the output of the fiber and the sample, so that the beam of light (dashed line 308) is scanned laterally (in x and y) over the region of the sample to be imaged. Light scattered from the sample is collected, typically into the same fiber 305 used to route the light for illumination. Reference light derived from the same source 301 travels a separate path, in this case involving fiber 303 and retro-reflector 304 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 302, to form light interference in a detector 320. Although a single fiber port is shown going to the detector, those skilled in the art recognize that various designs of interferometers can be used for balanced or unbalanced detection of the interference signal. The output signal from the detector 320 is supplied to a processing unit 321 that converts the observed interference into depth information of the sample. The results can be stored in the processing unit 321 or other storage medium or displayed on display 322. The processing and storing functions may be localized within the OCT instrument or functions may be performed on an external processing unit (e.g., the computer system 1200 shown in FIG. 12) to which the collected data is transferred. This unit could be dedicated to data processing or perform other tasks, which are quite general and not dedicated to the OCT device. The processing unit 321 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The interference causes the intensity of the interfered light to vary across the spectrum. The Fourier transform of the interference light reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system.

In FIG. 3, lens 323 is normally called the objective or ocular lens. It is present to produce a focused beam onto a desired part of the eye, in this case, the retina. In order to image the anterior segment (cornea, aqueous humor, and crystalline lens) and the posterior segment (vitreous humor and the various retinal tissues down to the sclera), the lens 323 needs to have its focal length adjusted. There are a variety of ways to achieve this, but often a method is to insert or add a negative lens at a position just downstream of its rear vertex 324. Such a lens could be added manually by the user and attached to the system via magnets or any other attachment mechanisms known to one skilled in the art. Thus, in this particular approach, addition of this lens to the optical configuration of the system permits the instrument to switch between anterior and posterior imaging.

Figure 1:
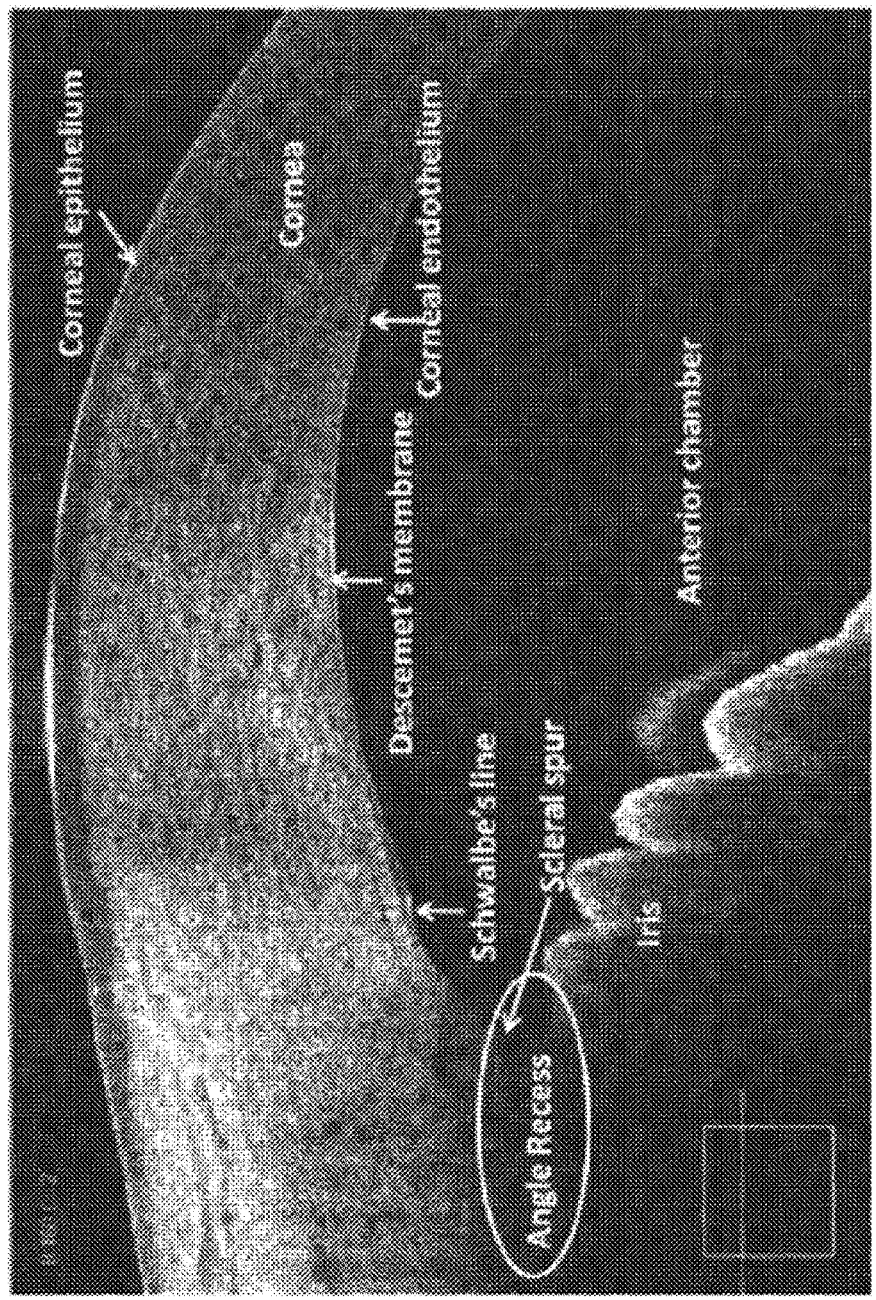
FIG. 1 is an exemplary HD-OCT image showing locations of certain landmarks in the anterior chamber of an eye.
Figure 2:
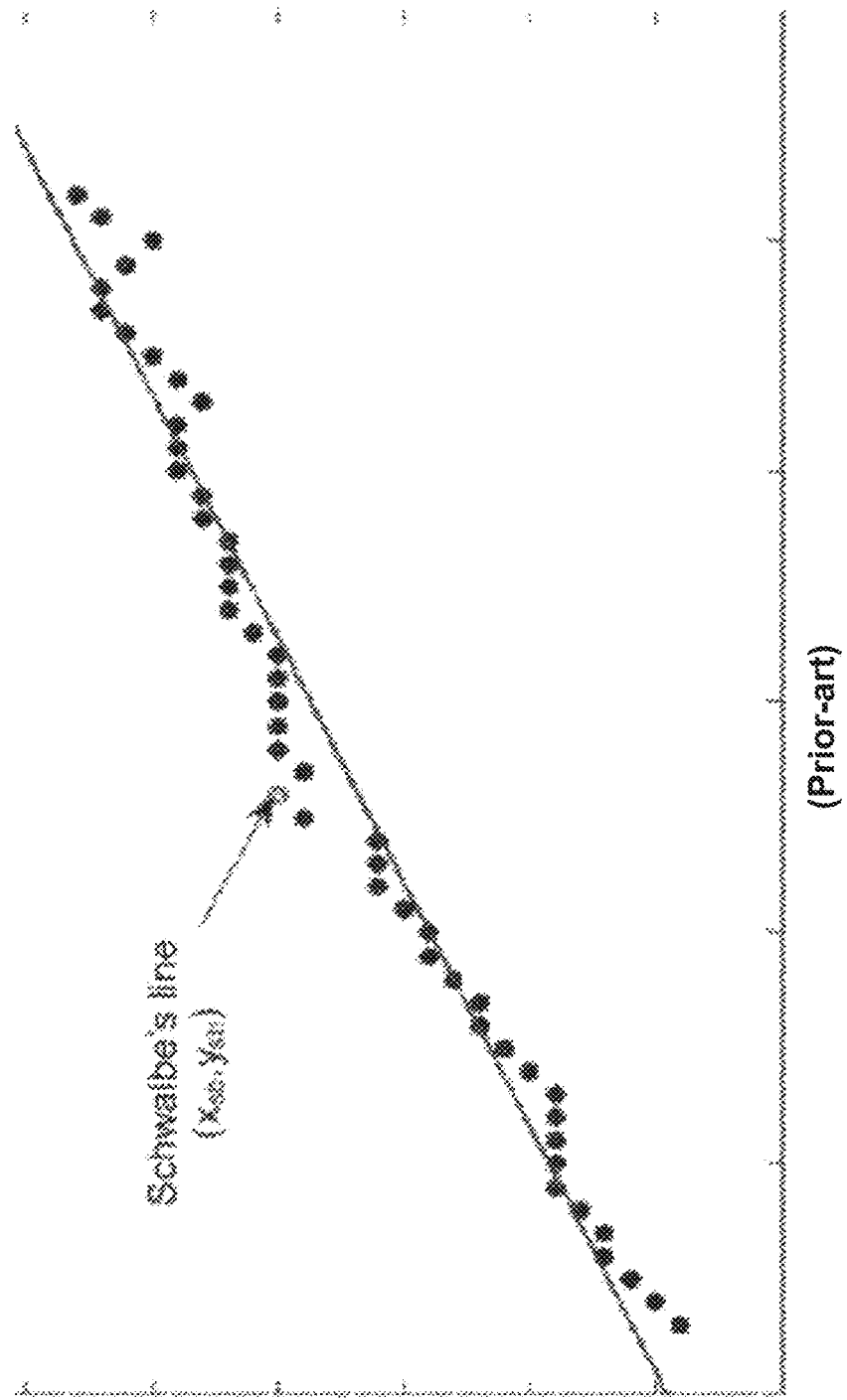
FIG. 2 illustrates a prior-art method of identifying the Schwalbe's line.

Commercial OCT devices exist for imaging both the anterior and posterior sections of the eye. Some of these are, for example, Zeiss Cirrus™ HD-OCT, Visante™ Omni, and Stratus™ (Carl Zeiss Meditec, Inc. Dublin, Calif.)). The Cirrus™ HD-OCT system allows for imaging both the anterior and posterior regions by inserting a lens to change the focal properties of the system as described in U.S. Publication No. 2007/0291277. The Cirrus™ HD-OCT produces images of the anterior segment of an eye by using spectral domain optical coherence tomography (SD-OCT) technology. FIG. 1 shows an exemplary anterior segment HD-OCT image.

As noted earlier, the scleral spur has often been used as a landmark when measuring anterior chamber angle characteristics and distinguishing between open and narrow or closed angles. However, in SD-OCT high-definition images of the angle (HD-Angle) images, Schwalbe's line is often more consistently visualized than the scleral spur (as shown for example in FIG. 1) and has been proposed herein as an independent landmark for measuring the angle. Schwalbe's line is the anatomical line found on the posterior surface of the cornea and delineates the outer limit of the corneal endothelium layer. Specifically, it represents the termination of Descemet's membrane. Schwalbe's line appears as a point in an HD-Angle image.

It may not be feasible to robustly segment the endothelium layer as well as the termination of Descemet's membrane in an HD-Angle image. However, based on observation, it may be possible to measure several low level as well as high level features around and on the Schwalbe's line in the image. Some of these features may include, for example, local maximum curvature at posterior corneal surface, local contrast changes, and high brightness values, etc. Based on these features, an algorithm is proposed in the present application to automatically detect the Schwalbe's line position. The basic idea is to identify Schwalbe's line in OCT images by evaluating the features at local curvature maxima of the curvature function of the poster corneal surface segmentation. The location of a local maximum that maximizes a total cost function is considered as the Schwalbe's line location. The total costs are calculated based on a series of costs derived from observed features such as curvature values as well as image content at local curvature maxima. The details of the algorithm are discussed in further detail below.

Schwalbe's Line Detection Algorithm

Figure 4:
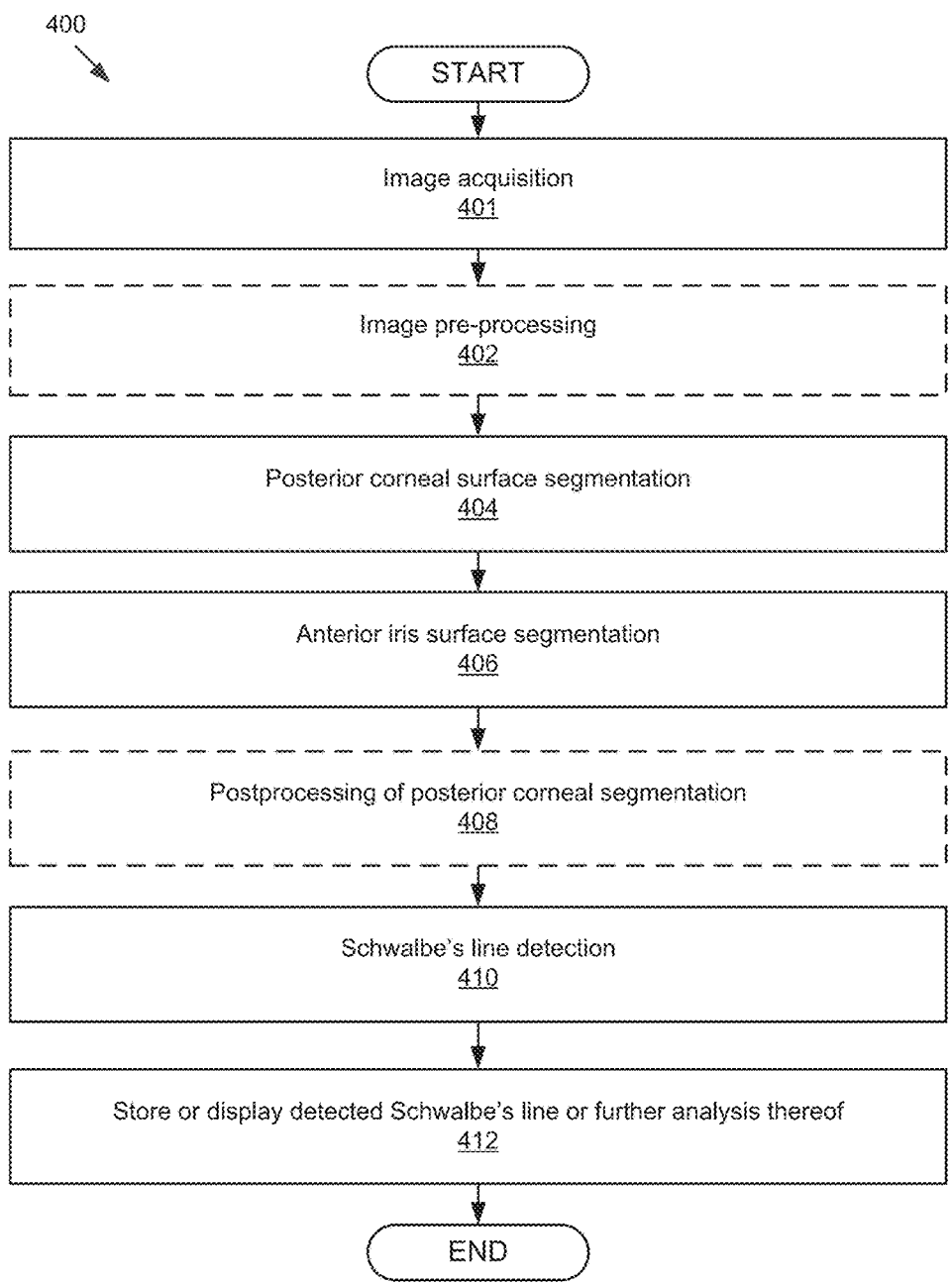
FIG. 4 is a flowchart of a generalized method for Schwalbe's line detection.

The basic steps of the algorithm are shown in method 400 in FIG. 4. These steps are as follows:

Step 401: Image Acquisition

In this step, OCT measurements of the anterior segment of an eye are acquired (for example, using the OCT system 300 described with respect to FIG. 3) and then an OCT image is generated from the acquired measurements. The generated OCT image is an angle image including a corneal posterior surface and an iris anterior surface.

Step 402: HD-Angle Image Preprocessing

It should be noted that box 402 is showed with dotted lines to indicate that it is an optional step and may not be performed at all times in the method 400. Often an angle image contains features such as dark shadows, unsmooth features, and holes within stroma, sclera, and iris regions. To make these regions uniform and homogenous, optional pre-processing such as using a flood fill operation (filling holes) followed by a Bilateral-filtering can be applied to the angle image. The filling holes operation fills holes in the input image (see for example, Soille, P., Morphological Image Analysis: Principles and Applications, Springer-Verlag, 1999, pp. 173-174). A hole is a set of dark background pixels that are enclosed by brighter pixels in a gray-scale image.

Also, there may be a need to smooth the stromal and iris regions to minimize the segmentation failures. A bilateral filter can be used to preserve the edges and reduce noise at the same time (see for example, Carlo Tomasi and Roberto Manduchi, "Bilateral filtering for gray and color images," in Computer Vision, 1998. Sixth International Conference on. IEEE, 1998, pp. 839-846).

Step 404: Posterior Corneal Surface Segmentation

This step involves segmenting the posterior corneal surface using one or more segmentation approaches. In some embodiments, due to diversity in image quality and accuracy requirement of posterior segmentation (because of saddle curvature change at Schwalbe's line position), the posterior corneal segmentation may fail if a single segmentation method/approach is used. Combining two segmentation approaches (e.g., graph-based and binary-based) may lead to more robust segmentation approach. However, it should be understood that the step 404 is also possible using only one segmentation approach and is not in any way limited to using the two specific approaches as discussed below. In some embodiments, whether the second segmentation approach should be used depends upon a confidence level in the first segmentation approach, which is discussed later below. For instance, if the confidence level is determined to be low, then the second segmentation approach may be required otherwise the first segmentation approach is enough for segmenting the posterior corneal surface. Segmenting the posterior corneal surface using the optional two segmentation approaches involves the following:

1) Region of interest (ROI) extraction: as noted above, for an accurate segmentation, two approaches such as the graph-based and binary-based segmentations are performed. An initial ROI can be extracted from the preprocessed angle image where the Schwalbe's line is expected to be located. To limit the ROI for the segmentation, some of the pixel values above and/or below a flexible sigmoid fit of the anterior corneal surface segmentation can be modified (e.g., removed, shifted, and/or adjusted) (see for example, US Publication Nos. 2013/30188140 and 2013/0208240).

2) Graph-based segmentation: After the ROI containing surface of interest (i.e., area around Schwalbe's line) is identified, graph-based segmentation can be performed within the ROI. This segmentations works well on a total cost function. The local cost functions are derived, for instance, from the image gradient magnitude in A-scan direction and intensity image. Local cost is the cost assigned to every single pixel in the ROI. The pixels that most likely belong to the surface will be assigned low cost and vice versa (see for example, S. Timp, "A new 2D segmentation method based on dynamic programming applied to computer aided detection in mammography," Med. Phys. 31(5): 958-71 (2004)). The total cost function is computed based on weighted sum of a series of costs such as the axial gradient image and normalized intensity image, etc.

In some embodiments, some segmentation points at the total cost image are removed due to low confidence level. For instance, once the graph-based segmentation is performed, confidence values (e.g., ranging from 0 to 1) are assigned to each segmentation point to evaluate the confidence in the segmentation, and if the confidence value for a segmentation point is smaller than a certain threshold, that point is removed from the segmentation.

3) Binary-based segmentation: the segmentation from step 2) may be, in some instances, fragmented or not complete due to low confidence level of segmentation in the posterior surface. A binary-based segmentation combined with the graph-based segmentation may lead to more robust posterior segmentation. Here, a morphological reconstruction approach is used (see for example, Vincent, L., "Morphological Grayscale Reconstruction in Image Analysis: Applications and Efficient Algorithms," IEEE Transactions on Image Processing, Vol. 2, No. 2, April, 1993, pp. 176-201). This approach performs morphological reconstruction of the image marker under the image mask. The mask is generated by thresholding the total cost image. Any pixel value greater than or equal to a threshold is set to zero. All other pixels are set to one. The marker is generated by setting the pixel values at the segmentation results obtained in step 2).

4) Combining two segmentation approaches: In this step, the graph-based and binary-based segmentations are combined to construct a segmentation result with high confidence. The posterior segmentation points that were missing in step 2) are taken from the segmentation result in step 3).

Step 406: Anterior Iris Surface Segmentation

This step involves segmenting the anterior iris surface using one or more iterations of the graph-based segmentation discussed above.

Finding a division boundary between the cornea/sclera and the iris that extends the posterior segmentation to the trabecular meshwork and sclera boundaries, leads to more robust segmentation of the anterior iris surface. The same graph-based segmentation and cost images described in sub-step 2) of posterior corneal surface segmentation (step 404) can be used to segment the division boundary between the cornea/sclera. The division boundary is calculated by offsetting the combined segmentation of the posterior and sclera segmentation after smoothing.

Step 408: Post-Processing of Posterior Corneal Segmentation

The Schwalbe's line is located on the posterior surface above trabecular meshwork. Trabecular meshwork outer boundary often appears blurry in HD-Angle images. Therefore, the posterior segmentation may not perform well in trabecular meshwork region. Another problem is that the segmentation might extend to the outer sclera boundary. To limit the segmentation around the Schwalbe's line, a post-processing step may be required. For this, the posterior segmentation points smaller than certain microns (e.g., 200 microns) to the iris segmentation at the same lateral position are removed. These segmentation points most likely belong to the sclera and trabecular meshwork boundaries. It should be recognized that the step 408 is shown with dotted lines in FIG. 4 to indicate that the post-processing step is optional and may not be part of the method 400 at all times and processing.

Step 410: Schwalbe's Line Detection

Figure 5A:
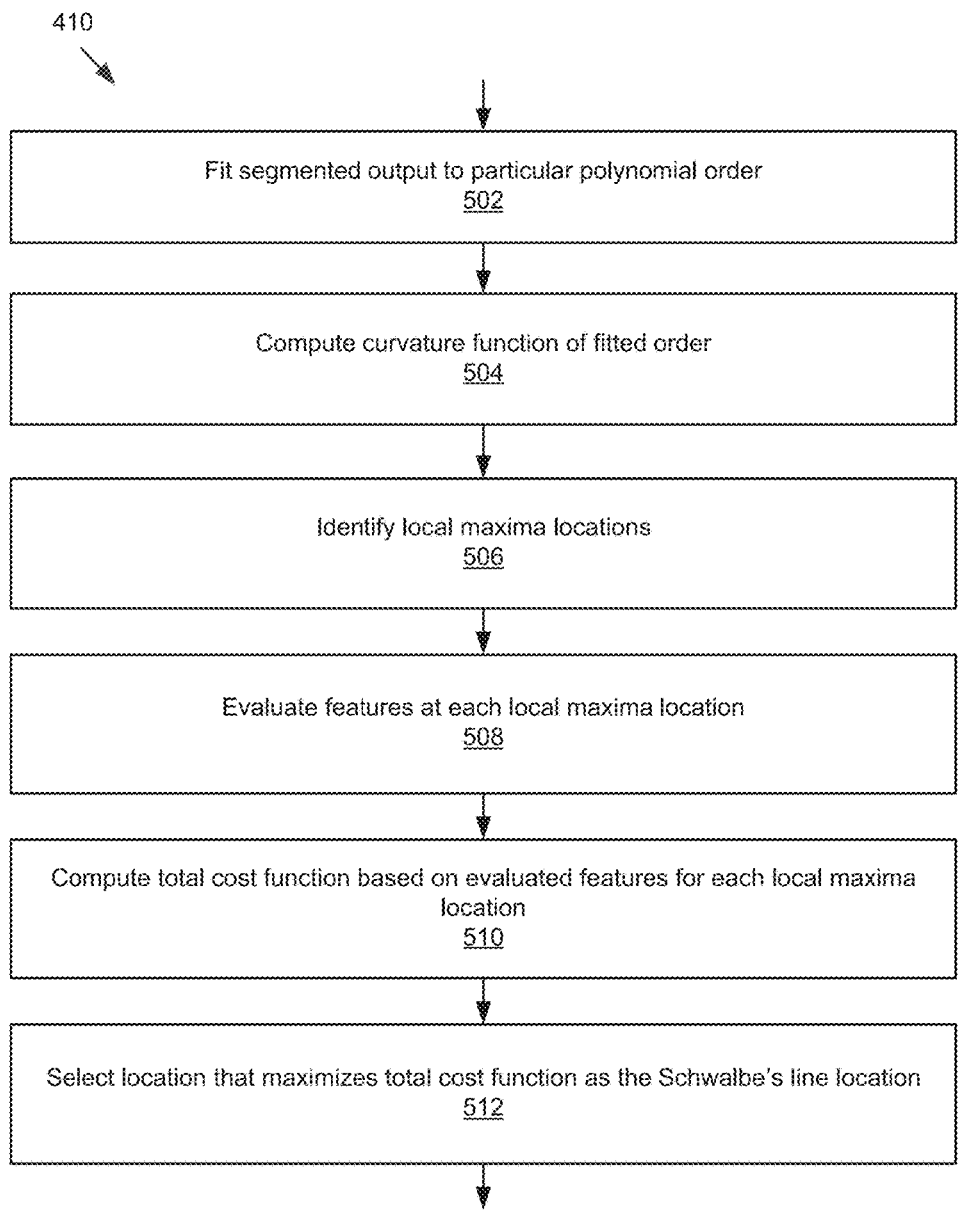
FIG. 5A is a flowchart of one example method for identifying the Schwalbe's line location.
Figures 7A, 7B:
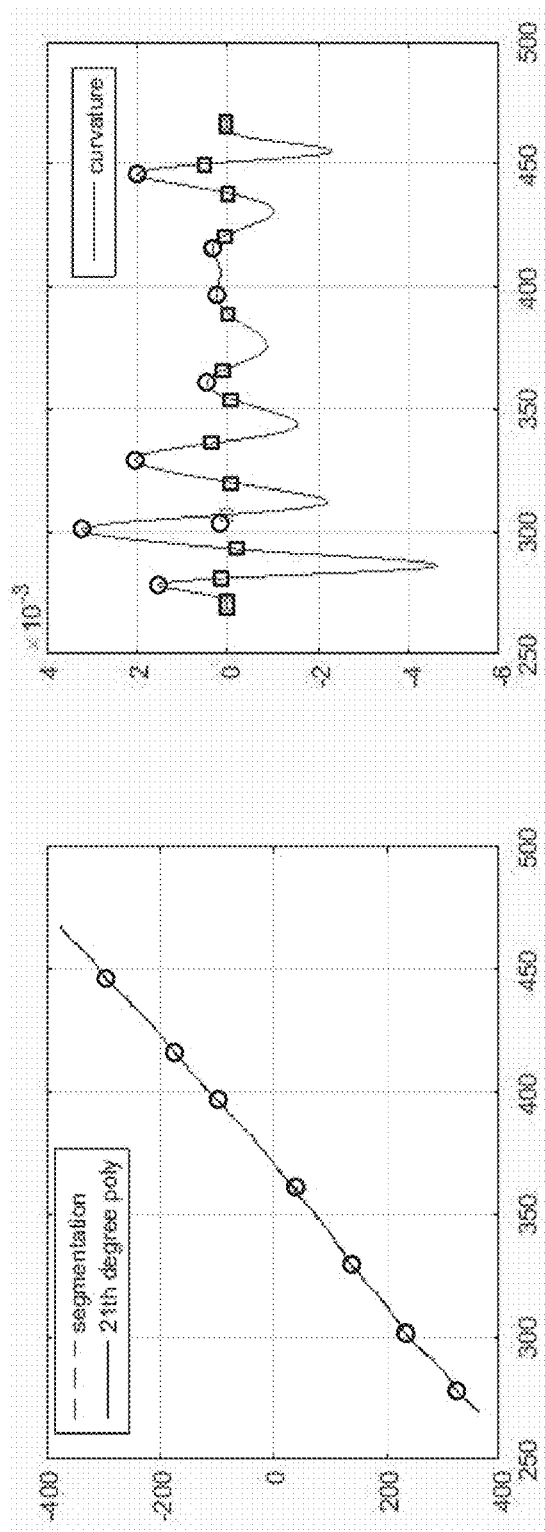
FIG. 7A illustrates an example fitting of a segmented output to a particular polynomial order (e.g., 21th order polynomial).
FIG. 7B depicts local curvature maxima locations (indicated by circles) and inflection points (indicated by rectangles) after computing a curvature function of the fitting illustrated in FIG. 7A.

As mentioned elsewhere herein, one embodiment for identifying the Schwalbe's line includes evaluating various features at local curvature maxima of the curvature function of the posterior corneal surface segmentation. One of the locations of local curvature maxima with highest total cost function can be considered as the Schwalbe's line location. The total costs are calculated based on a series of weighted costs derived from computed features. This embodiment is further described with respect to FIG. 5A, which includes the following steps:

1) Fit segmented output to a particular order polynomial (step 502): here, a particular degree of polynomial is determined from a plurality of different degree polynomials based on one or more metrics and then fitted to the segmented output/result (i.e., obtained in step 408). An exemplary metric for determining the particular polynomial order/degree among a plurality of different polynomial orders is its accuracy and/or success rate in automatically identifying the Schwalbe's line location in the past. For instance, for determining the particular order polynomial, the different polynomial orders were applied to a given segmentation for identifying the Schwalbe's line location and the identification of each was then compared with an expert's manual identification of the Schwalbe's line. The polynomial order with the highest success rate or its identification most closely matched with the expert's manual identification is determined as the particular order polynomial for the fitting. FIG. 7A shows an exemplary fitting of a 21th order polynomial to the posterior segment.

2) Compute curvature function of the fitted order (step 504): a curvature function of the posterior segment fit of step 1) is determined by the curvature equation:

$$\kappa = \frac{y''}{(1 + y'^2)^{3/2}}$$

Where, y is posterior fit, y' is first derivative of y, and y" is second derivative of y.

3) Identify local curvature maxima locations (step 506): once the curvature function is computed, all peaks with a curvature value greater than a certain threshold value are identified as locations of local curvature maxima. Also, inflection points are determined by finding the zero-crossing (i.e., point in the curve where the curvature direction changes). FIG. 7B shows the curvature function of the fitting depicted in FIG. 7A, where local curvature maxima are marked with circles and approximate inflection points are marked with rectangles.

4) Compute features at each local curvature maxima location (step 508): examples of features can be as follows:
Curvature values at local curvature maxima
Distance between two adjacent inflection points
Distance of maxima location to a linear fit of the posterior segment
Sum of absolute gradient in axial direction in ROI extracted at maxima
Gradient image pixel distribution in ROI
Area around the maxima location 5) Compute total cost function based on extracted features for each local curvature maxima location (step 510): The total cost function is calculated by weighted summation of extracted feature values at maxima locations.

6) Select location that maximizes total cost function as the Schwalbe's line location (step 512): Once the total cost function is computed for each maxima location as discussed in step 5), the location with the highest cost or the location that maximizes the total cost is selected to be associated with the Schwalbe's line location on the posterior surface.

In some implementations, following step 506 (i.e., identifying local curvature maxima locations), a machine learning or specifically a deep learning approach can identify the Schwalbe's line. For instance, the local maxima associated with Schwalbe's line can be labeled by experts. Then the regions around the identified local curvature maxima locations in a training set can be used to train a network (e.g. convolutional neural network). The training set contains both the local curvature maxima locations labeled as Schwalbe's line (positive) and the ones that are labeled as negative. For instance, a two-class neural network to create a neural network model is built that can be used to predict two probability values for a given data at local curvature maximum. The value with higher probability is associated with Schwalbe's line. An alternative approach is to model a neural network for an one-class classification problem which tries to identify Schwalbe's line by learning from a training set containing only labeled data associated with Schwalbe's line.

In some implements, following step 508 (i.e., evaluating features at each local maxima locations), other supervised machine learning approaches such as support vector machine (SVM) and random forest, etc. can be used to solve the classification problem. For instance, given a training set (a set of feature vectors with the elements of the extracted features at a local maxima; containing both the ones associated with Schwalbe's line and the ones that are labeled as negative, a SVM training algorithm builds a model that assigns a new feature vector at a given local maximum to Schwalbe's line category, making it a binary linear classifier.

Figure 8:
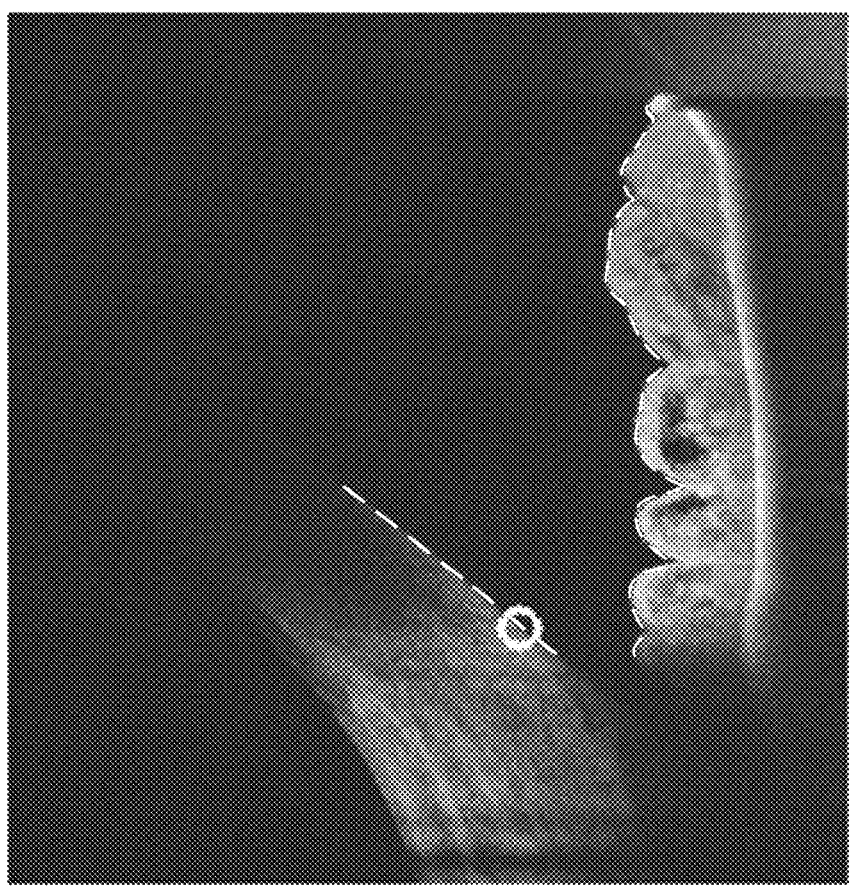
FIG. 8 is an example image showing location of the Schwalbe's line (white circle) detected using the algorithm discussed herein.
Figure 9:
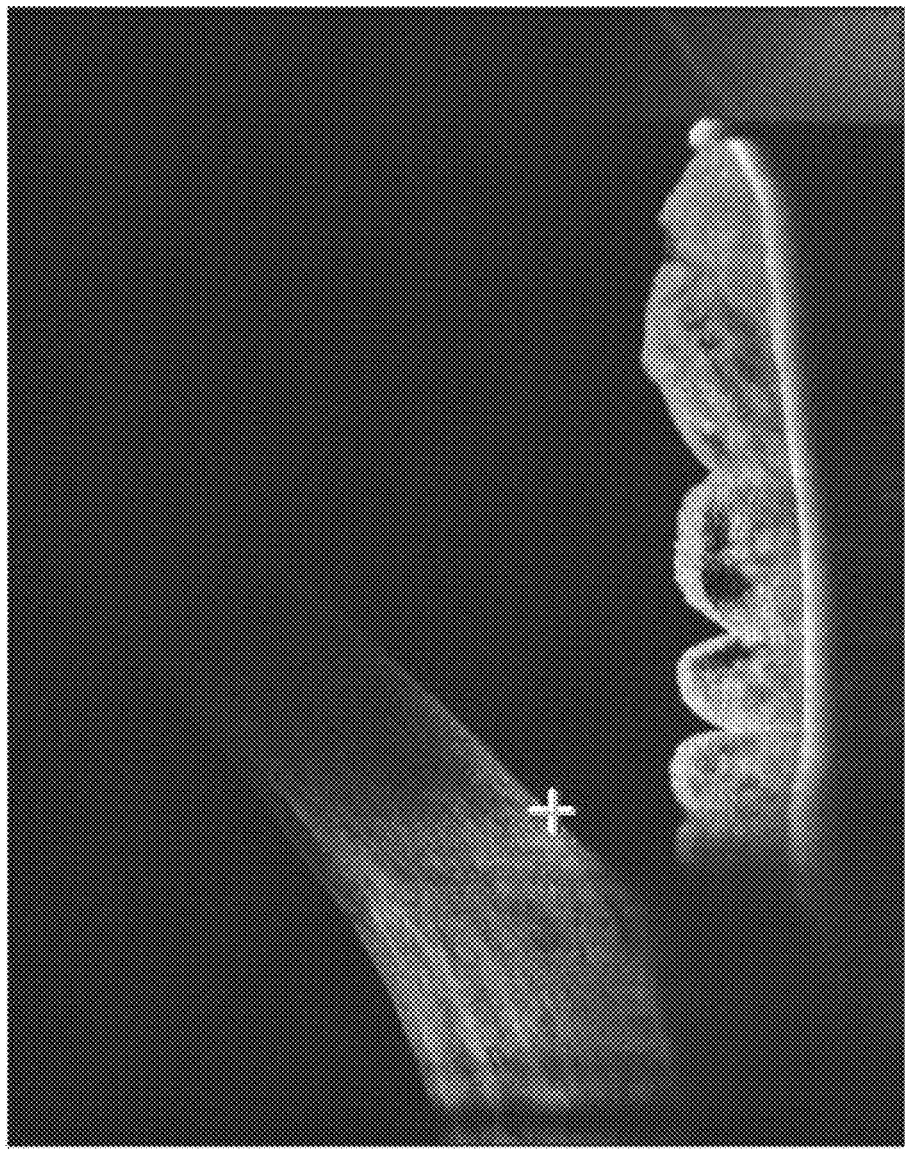
FIG. 9 is an example image showing location of the Schwalbe's line automatically determined by the algorithm (gray cross) vs. a location manually identified by an expert user (white cross).

FIG. 8 shows an example image with the location of Schwalbe's line (indicated by white circle) detected by the algorithm discussed herein. FIG. 9 shows a comparison of the location of Schwalbe's line as automatically determined by the algorithm (indicated by gray cross) and the location as manually identified by an expert grader (indicated by white cross substantially underlying but slightly displaced from the gray cross). As seen, it can be noted that the Schwalbe's line detection algorithm discussed in the present application is very accurate in automatically identifying the Schwalbe's line location (within 100 µm of the expert's manual identification).

Figure 5B:
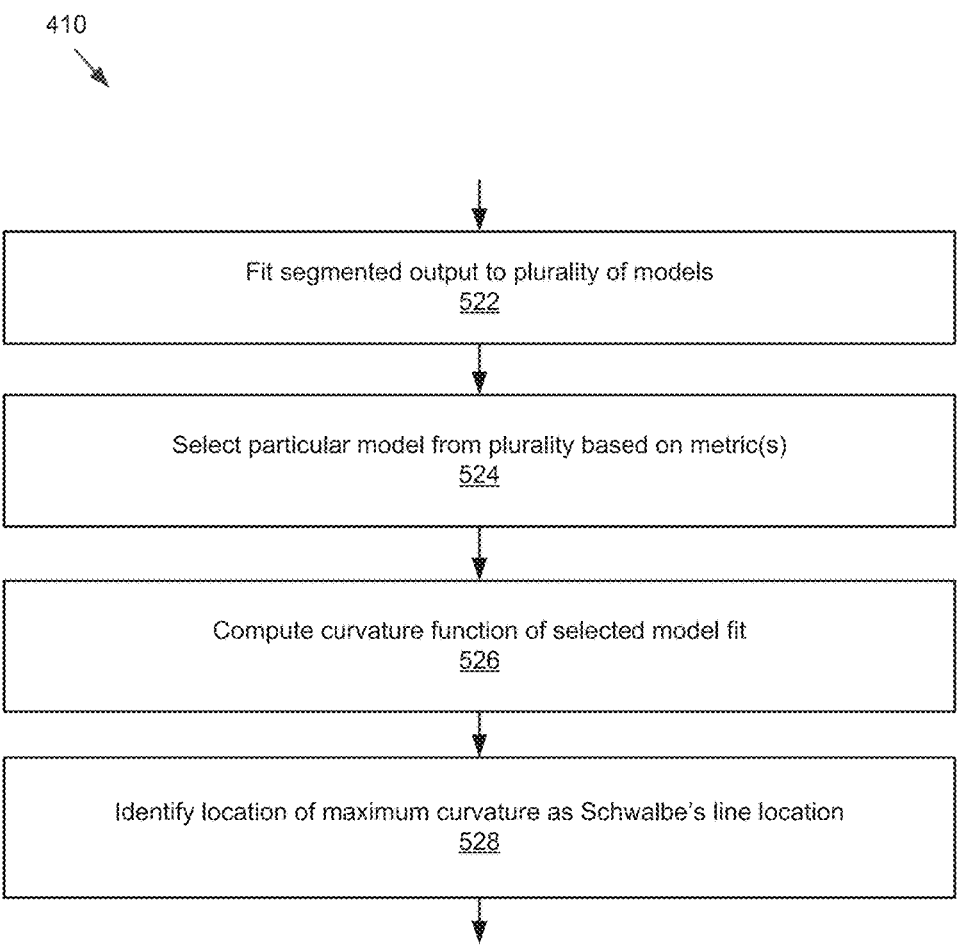
FIG. 5B is a flowchart of a second example method for identifying the Schwalbe's line location.
Figure 5C:
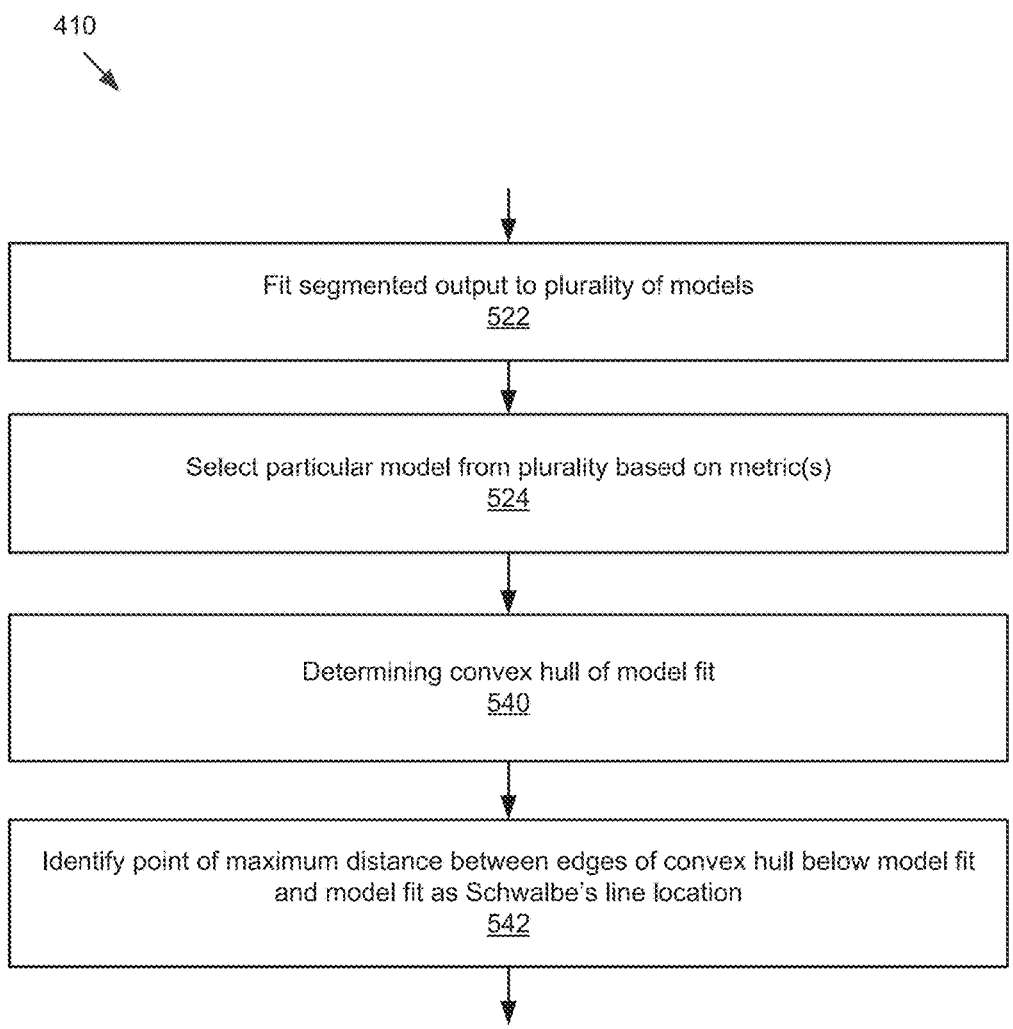
FIG. 5C is a flowchart of a third example method for identifying the Schwalbe's line location.
Figure 6:
FIG. 6 is an example of a segmented image generated after segmenting the posterior corneal surface and the anterior iris surface in an HD-angle image.
Figure 10A:
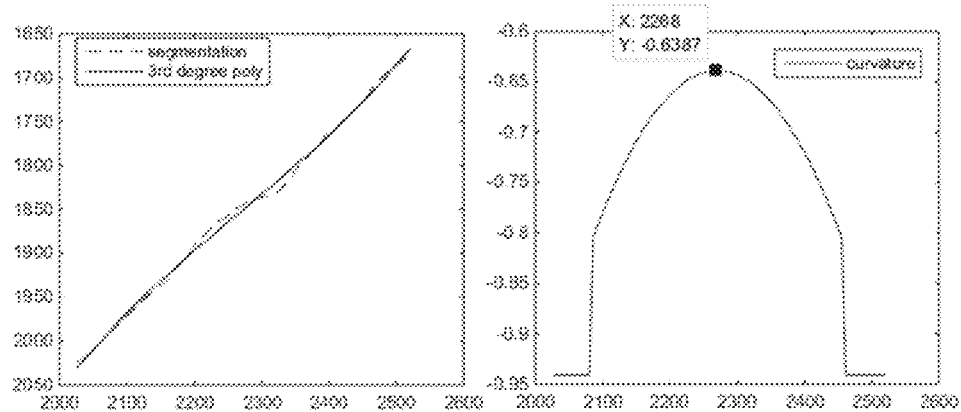
FIGS. 10A-10C illustrate curvature functions upon applying different degree polynomials to a segmentation. In particular.
Figure 10B:
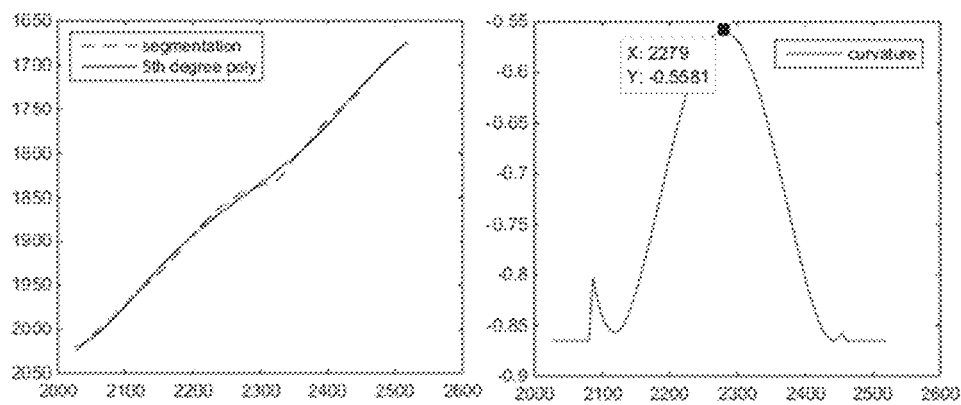
Figure 10C:
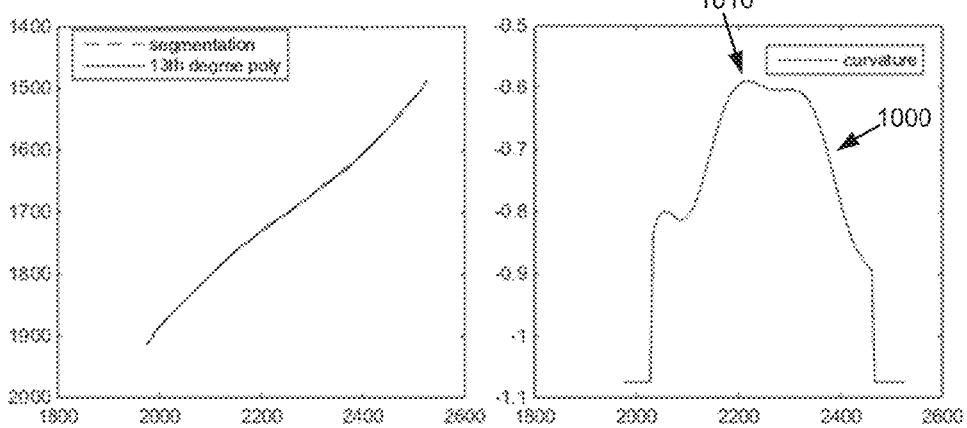

FIGS. 5B and 5C illustrate two additional embodiments/methods for Schwalbe's line detection. In particular, FIG. 5B illustrates an embodiment/method of identifying the Schwalbe's line location based on a location of maximum curvature. FIG. 5C illustrates an embodiment/method of identifying the Schwalbe's line location based on a maximum distance to convex hull of the posterior segment fit. It should be noted that these methods, in some implementations, are part of the method 400 and begin performing their functionalities/operations (i.e., from step 522) after completion of step 408 in method 400 (see FIG. 4). In other implementations, these methods are separate entities and/or may be part of a different process/method. It should further be noted that likewise or similar reference numerals are used in these methods (FIGS. 5B and 5C) to refer to the same operation or functionality. These methods are discussed in detail below:

With reference to FIG. 5B, the method of finding Schwalbe's line includes first, fitting the segmented output (i.e., posterior corneal segmentation obtained in step 408) to a plurality of models (step 522). The fitting method, in some implementations, can be a robust regression (e.g., Random sample consensus (RANSAC)) to exclude outliers (e.g., segmentation error(s)). The plurality of models discussed herein may include, for example and without limitation, different degree of polynomials, piecewise spline, etc. By way of example, FIGS. 10A-C show fittings of different degree polynomials to a given segmentation and their corresponding computed curvature functions. In particular, FIG. 10A shows fitting of a $3^{rd}$ degree polynomial to the segmentation; FIG. 10B shows fitting of a $5^{th}$ degree polynomial to the segmentation; and FIG. 10C shows fitting of a $13^{th}$ degree polynomial.

Next, in step 524, a particular model from the plurality of models is selected for the Schwalbe's line detection. The particular model is selected among the plurality based on one or more metrics. For instance, the model is selected based on its prior success rate in accurately identifying the Schwalbe's line compared to the other models, as discussed in detail with respect to 1) of step 410 above. Some other metrics for selecting a model may include, for example, best fitting to the segmentation with the least segmentation error, previously calculated and learned data upon applying the different models to a similar segmentation, etc.

Once the model is selected in step 524 and fitted to the segmented output, a curvature function of the model fit is computed (step 526) using the equation discussed in sub-step 2) of step 410 above. In step 528, the location of maximum curvature (i.e., highest peak in the curve) is identified as an approximate location of Schwalbe's line. By way of an example and with reference to FIGS. 10A-C, it has been observed that the $13^{th}$ degree polynomial (shown in FIG. 10C) is the best suitable model among the other models (i.e., $3^{rd}$ degree and $5^{th}$ degree polynomials) for the fitting and the Schwalbe's line detection. Reference numeral 1000 shows the curvature upon computing the curvature function of the model fit and reference numeral 1010 shows the point/location of maximum curvature, which is thereby identified as the Schwalbe's line location.

Figure 11:
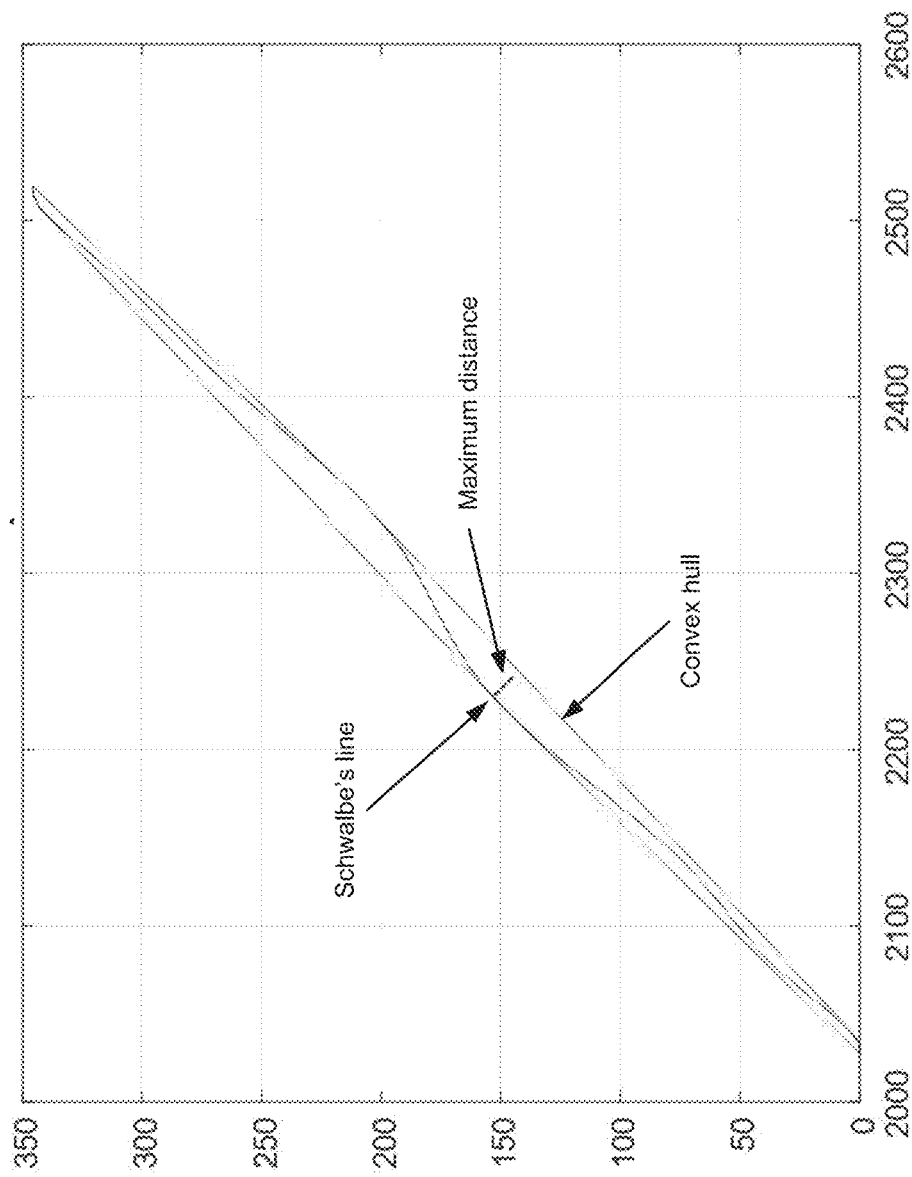
FIG. 11 is an example plot showing convex hull of a posterior fit that is used as a basis for Schwalbe's line detection according to one aspect of the present invention.

With reference to FIG. 5C, the method of finding the Schwalbe's line based on a maximum distance to convex hull of the posterior segment fit includes steps of fitting the posterior segment to a plurality of models (step 522) and then selecting a model from the plurality (step 524) as discussed with respect to FIG. 5B. In step 540, the convex hull of the selected model fit is determined and then in step 542, the maximum distance to convex hull of the model fit is used as a basis for identifying the location of Schwalbe's line. For instance, the point of maximum distance is identified as the Schwalbe's line location. The point of maximum distance is determined from the convex hull edges below the model fit only, as shown for example in FIG. 11.

Figure 12:
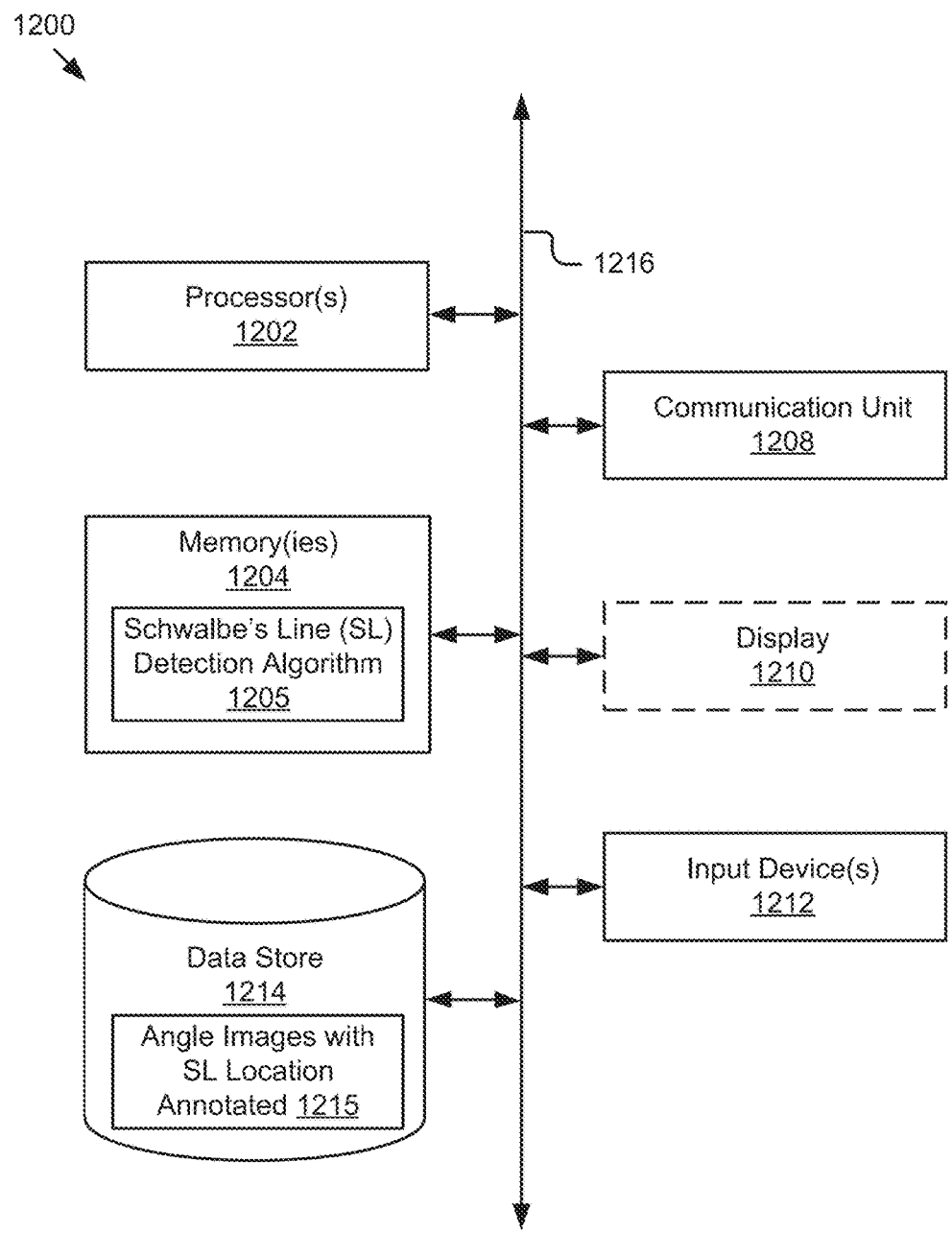
FIG. 12 is a block diagram of an example computer system configured to perform the functions discussed in the present application.

Step 412: Store or Display Detected Schwalbe's Line or Further Analysis Thereof In this step, the identified Schwalbe's line location, as discussed above with respect to FIGS. 5A-5C, is stored in a data store (e.g., the data store 1214 shown in FIG. 12) for future reference, access, and/or retrieval, or provided for display to a user, such as an expert grader for further analysis on a display (e.g., the display 322 (FIG. 3) or the optional display 1210 (FIG. 12). The step 412 is advantageous as the user using the identified Schwalbe's line location can determine the anterior chamber angle or Iridocorneal angle (see for example, Qin, B., et al. (2013). "Anterior chamber angle measurements using Schwalbe's line with high-resolution fourier-domain optical coherence tomography." *J Glaucoma* 22(9): 684-688), and decide suitability of one or more implanatable devices within the angle for the treatment of glaucoma, such as angle-closure glaucoma, in patients. The step is further advantageous as the identified Schwalbe's line location stored in the data store (e.g., angle images with Schwalbe's line location annotated 1215 in the data store 1214) can be used to further train the algorithm discussed herein for even more accurate and precise detection in the future. For instance, the algorithm can be trained using the identified Schwalbe's line location and any previously identified locations to automatically, quickly, and accurately identify where the Schwalbe's line should be located in an anterior chamber angle image.

It should be understood that the methods described herein (with respect to FIG. 4 and FIGS. 5A-5C) are not limited to the steps and/or operations embodied by them and that other steps and/or operations are also possible and are within the scope of the present disclosure.

Example Computer System

The processing unit 321 that has been discussed herein in reference to FIG. 3 can be implemented with a computer system configured to perform the functions that have been described herein for this unit. For instance, the processing unit 321 can be implemented with the computer system 1200, as shown in FIG. 12. The computer system 1200 may include one or more processors 1202, one or more memories 1204, a communication unit 1208, an optional display 1210, one or more input devices 1212, and a data store 1214. The display 1210 is shown with dotted lines to indicate it is an optional component, which, in some instances, may not be a part of the computer system 1200. In some embodiments, the display 1210 discussed herein is the display 322 that has been discussed herein in reference to FIG. 3.

The components 1202, 1204, 1208, 1210, 1212, and 1214 are communicatively coupled via a communication or system bus 1216. The bus 1216 can include a conventional communication bus for transferring data between components of a computing device or between computing devices. It should be understood that the computing system 1200 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 1202 may execute various hardware and/or software logic, such as software instructions, by performing various input/output, logical, and/or mathematical operations. The processor(s) 1202 may have various computing architectures to process data signals including, for example, a complex instruction set computer (CISC) architecture, a reduced instruction set computer (RISC) architecture, and/or architecture implementing a combination of instruction sets. The processor(s) 1202 may be physical and/or virtual, and may include a single core or plurality of processing units and/or cores. In some embodiments, the processor(s) 1202 may be capable of generating and providing electronic display signals to a display device, such as the display 1210, supporting the display of images, capturing and transmitting images, performing complex tasks including various types of feature extraction and sampling, etc. In some embodiments, the processor(s) 1202 may be coupled to the memory(ies) 1204 via a data/communication bus to access data and instructions therefrom and store data therein. The bus 1216 may couple the processor(s) 1202 to the other components of the computer system 1200, for example, the memory(ies) 1204, the communication unit 1208, or the data store 1214.

The memory(ies) 1204 may store instructions and/or data that may be executed by the processor(s) 1202. In the depicted embodiment, the memory(ies) 1204 stores at least the Schwalbe's line (SL) detection algorithm 1205, which may include software, code, logic, or routines for automatically identifying the Schwalbe's line location as discussed elsewhere herein. For instance, the Schwalbe's line detection algorithm 1205 may perform all or some of the steps depicted in FIG. 4 and FIGS. 5A-5C. In some embodiments, the memory(ies) 1204 may also be capable of storing other instructions and data including, for example, an operating system, hardware drivers, other software applications, databases, etc. The memory(ies) 1204 are coupled to the bus 1216 for communication with the processor(s) 1202 and other components of the computer system 1200. The memory(ies) 1204 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 1202. A non-transitory computer-usable storage medium may include any and/or all computer-usable storage media. In some embodiments, the memory(ies) 1204 may include volatile memory, non-volatile memory, or both. For example, the memory(ies) 1204 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 321 may include one or more computers or processing units at the same or different locations. When at different locations, the computers may be configured to communicate with one another through a wired and/or wireless network communication system, such as the communication unit 1208. The communication unit 1208 may include network interface devices (I/F) for wired and wireless connectivity. For example, the communication unit 1208 may include a CAT-type interface, USB interface, or SD interface, transceivers for sending and receiving signals using Wi-Fi™; Bluetooth®, or cellular communications for wireless communication, etc. The communication unit 1208 can link the processor(s) 1202 to a computer network that may in turn be coupled to other processing systems.

The display 1210 represents any device equipped to display electronic images and data as described herein. The display 1210 may be any of a conventional display device, monitor or screen, such as an organic light-emitting diode (OLED) display, a liquid crystal display (LCD). In some embodiments, the display 1210 is a touch-screen display capable of receiving input from one or more fingers of a user. For example, the device 1210 may be a capacitive touch-screen display capable of detecting and interpreting multiple points of contact with the display surface.

The input device(s) 1212 are any devices for inputting data on the computer system 1200. In some embodiments, an input device is a touch-screen display capable of receiving input from one or more fingers of the user. The functionality of the input device(s) 1212 and the display 1210 may be integrated, and a user of the computer system 1200 may interact with the system by contacting a surface of the display 1210 using one or more fingers. In other embodiments, an input device is a separate peripheral device or combination of devices. For example, the input device(s) 1212 may include a keyboard (e.g., a QWERTY keyboard) and a pointing device (e.g., a mouse or touchpad). The input device(s) 1212 may also include a microphone, a web camera, or other similar audio or video capture devices.

The data store 1214 can be an information source capable of storing and providing access to data. In the depicted embodiment, the data store 1214 is coupled for communication with the components 1202, 1204, 1208, 1210, and 1212 of the computer system 1200 via the bus 1216, and coupled, via the processor(s) 1202, for communication with the SL detection algorithm 1205. As depicted, the data store 1214 stores at least a plurality of HD-angle images 1215 with Schwalbe's line location manually pre-identified and pre-annotated by an expert grader for training or learning purposes. For instance, the SL detection algorithm 1205 may be trained based on these manually pre-annotated SL location images to automatically predict in future where the Schwalbe's line is expected or supposed to be located given a HD-angle image. In some embodiments, the SL detection algorithm 1205 is configured to manipulate, i.e., store, query, update, and/or delete, data stored in the data store 1214 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method to automatically identify Schwalbe's line location in an optical coherence tomography (OCT) image of the anterior chamber of an eye, said method comprising:
    acquiring measurements of the eye with an OCT device;
    generating an OCT image from the measurements;
    segmenting the posterior corneal surface in the image by using one or more segmentation approaches to produce a segmented output;
    computing a curvature function based on the segmentation to identify a set of local curvature maxima locations;
    evaluating features at each local curvature maxima location;
    identifying the Schwalbe's line location using the evaluated features at each maxima location; and
    storing or displaying the identified Schwalbe's line location or a further analysis thereof.

2. The method of claim 1, wherein segmenting the corneal surface is preceded by identifying a region of interest where the Schwalbe's Line is expected to be located.

3. The method of claim 1, wherein identifying the Schwalbe's line location using the evaluated features at each maxima location comprises:
computing a total cost based on the evaluated features for each local curvature maxima location; and
identifying the location of local curvature maxima with highest cost as the Schwalbe's line location.

4. The method of claim 3, wherein computing the total cost comprises:
assigning a weight to each evaluated feature of a local curvature maxima location; and
summing each weighted feature of the local curvature maxima to calculate the total cost value of the features.

5. The method of claim 1, wherein the OCT image is an angle image including a corneal posterior surface and an iris anterior surface.

6. The method of claim 5, wherein the angle image is preprocessed to remove noise and make one or more anomalies in the image more uniform.

7. The method of claim 1, further comprising:
segmenting the anterior iris surface in the OCT image, wherein the segmented output is partially based on the result of the posterior corneal surface segmentation.

8. The method of claim 1 further comprising:
fitting the segmented output to a particular polynomial order, wherein computing the curvature function includes computing a curvature function of the fitted order.

9. The method of claim 8, wherein the particular polynomial order is selected from among a plurality of different polynomial orders based on 1) best fitting to the segmented output and 2) previously calculated and learned data upon applying the different polynomial orders to a similar segmented output.

10. The method of claim 1, wherein the local curvature maxima locations are peaks in the curve, said peaks having local curvature maxima in the curvature function of the curve.

11. The method of claim 1, wherein said method is trained based on a machine learning approach to automatically identify the Schwalbe's line location.

12. The method of claim 11, wherein the machine learning approach uses a large number of HD-Angle images with Schwalbe's line location annotated in each image.

13. The method of claim 1, further including the step of measuring the Iridocorneal angle based on the identification of the Schwalbe's line location.

14. The method of claim 13, wherein the measured Iridocorneal angle is further used for determining the suitability of implantable devices for the treatment of eye diseases in patients.

15. The method of claim 1 wherein the features that are evaluated at each local curvature maxima location are selected from one or more of:
(a) curvature values at local curvature maxima;
(b) distance between two adjacent inflection points;
(c) distance of maxima location to a linear fit of the posterior segment;
(d) sum of absolute gradient in axial direction in ROI extracted at maxima;
(e) gradient image pixel distribution in ROI; and
(f) area around the maxima location.

16. A method to automatically identify Schwalbe's line location in an optical coherence tomography (OCT) image of the anterior chamber of an eye, said method comprising:
acquiring measurements of the eye with an OCT device;
generating an OCT image from the measurements;
extracting a region of interest (ROI) in the OCT image where the Schwalbe's line is expected to be located;
segmenting the posterior corneal surface in the ROI by using one or more segmentation approaches to produce a segmented output;
fitting a plurality of different models to the segmented output;
selecting a model from the plurality that is best suitable for the Schwalbe's line identification based on one or more metrics, wherein the metrics are selected from the group consisting of 1) best fitting to the segmented output, 2) previously calculated and learned data upon applying the different models to a similar segmented output, and 3) model that is best suitable for the Schwalbe's line identification;
computing a curvature function of the selected model;
identifying the location of maximum curvature as the Schwalbe's line location; and
storing or displaying the identified Schwalbe's line location or a further analysis thereof.

17. The method of claim 16, wherein the plurality of different models include different orders of polynomials and/or a piecewise spline.

18. A method to automatically identify Schwalbe's line location in an optical coherence tomography (OCT) image of the anterior chamber of an eye, said method comprising:
acquiring measurements of the eye with an OCT device;
generating an OCT image from the measurements;
extracting a region of interest (ROI) in the OCT image where the Schwalbe's line is expected to be located;
segmenting the posterior corneal surface in the ROI by using one or more segmentation approaches to produce a segmented output;
fitting a plurality of different models to the segmented output;
selecting a model from the plurality that is best suitable for the Schwalbe's line identification based on one or more metrics; and
determining the convex-hull of the fit of the selected model;
identifying a point of maximum distance between the edges of the convex-hull below the model fit and the model fit as the Schwalbe's line location; and
storing or displaying the identified Schwalbe's line location or a further analysis thereof.

* * * * *

UNITED STATES PATENT AND TRADEMARK OFFICE
CERTIFICATE OF CORRECTION

PATENT NO. : 10,123,691 B1
APPLICATION NO. : 15/458393
DATED : November 13, 2018
INVENTOR(S) : Homayoun Bagherinia Page 1 of 1

It is certified that error appears in the above-identified patent and that said Letters Patent is hereby corrected as shown below:

In the Specification

In Column 10, Line 16, delete "maxima;" and insert -- maxima) --, therefor.

In Column 11, Line 53, delete "implanatable" and insert -- implantable --, therefor.

In the Claims

In Column 14, Line 67, in Claim 2, delete "Line" and insert -- line --, therefor.

Signed and Sealed this
Thirtieth Day of July, 2019

Andrei Iancu
*Director of the United States Patent and Trademark Office*